(12) United States Patent
Geraldes et al.

(10) Patent No.: US 8,372,582 B2
(45) Date of Patent: Feb. 12, 2013

(54) METHODS OF MODULATING METABOLIC MEMORY

(75) Inventors: Pedro Geraldes, Brookline, MA (US); George Liang King, Dover, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 159 days.

(21) Appl. No.: 12/375,901

(22) PCT Filed: Aug. 1, 2007

(86) PCT No.: PCT/US2007/075004
§ 371 (c)(1),
(2), (4) Date: Feb. 26, 2010

(87) PCT Pub. No.: WO2008/016996
PCT Pub. Date: Feb. 7, 2008

(65) Prior Publication Data
US 2010/0160412 A1    Jun. 24, 2010

Related U.S. Application Data

(60) Provisional application No. 60/821,119, filed on Aug. 1, 2006, provisional application No. 60/945,865, filed on Jun. 22, 2007.

(51) Int. Cl.
*C12Q 1/68*    (2006.01)
(52) U.S. Cl. .............. 435/6; 435/325; 435/375
(58) Field of Classification Search .......... None
See application file for complete search history.

(56) References Cited

U.S. PATENT DOCUMENTS

| | | | |
|---|---|---|---|
| 6,121,047 A | 9/2000 | Bennett et al. | |
| 7,977,320 B2 | 7/2011 | Ball et al. | |
| 8,030,013 B2 | 10/2011 | Llovet et al. | |
| 8,168,602 B2 | 5/2012 | DePinho et al. | |

OTHER PUBLICATIONS

Geraldes et al. Nature Medicine 2009, vol. 15:No. 11 pp. 1298-1307.*
Shultz et al., "Severe defects in immunity and hematopoiesis caused by SHP-1 protein-tyrosine-phosphatase deficiency," TIBTECH, 15:302-307 (1997).
Wang et al., "Antagonism or Synergism," The Journal of Biological Chemistry, 281:21878-21883 (2006).
Krotz et al., "The Tyrosine Phosphatase, SHP-1, Is a Negative Regulator of Endothelial Superoxide Formation," Journal of the American College of Cardiology, 45:1700-6 (2005).
Yu et al., "SHP-1 Associates with Both Platelet-derived Growth Factor Receptor and the p85 Subunit of Phosphatidylinositol 3-Kinase," The Journal of Biological Chemistry, 273:3687-3694 (1998).
Boyka Markova et al., "Identification of Protein Tyrosine Phosphatases Associating with the PDGF Receptor," Biochemistry, 42:2691-2699 (2003).
Tao et al., "Comparison of the Signaling Mechanisms by which VEGF, $H_2O_2$, and Phosphatase Inhibitors Activate Endothelial Cell ERK1/2 MAP-kinase," Microvascular Research, 69:36-44 (2005).
Arikawa et al., "Effects of Insulin Replacements, Inhibitors of Angiotensin, and PKCβ's Actions to Normalize Cardiac Gene Expression and Fuel Metabolism in Diabetic Rats," Diabetes, 56:1410-1420 (2007).
Rask-Madsen and King, "Mechanisms of Disease: Endothelial Dysfunction in Insulin Resistance and Diabetes," Nature Clinical Practice Endocrinology & Metabolism, 3:46-56 (2007).
Geraldes, Pedro, et al., "Activation of Protein Kinase C Isoforms and Its Impact on Diabetic Complications," Circulation Res. 106:1319-1331 (2010).

* cited by examiner

*Primary Examiner* — Kimberly Chong
(74) *Attorney, Agent, or Firm* — Pierce Atwood LLP; Joseph M. Maraia; Kevin M. Farrell

(57) ABSTRACT

Described are methods of identifying modulators of metabolic memory, for the treatment of microvascular complications of diabetes, as well as methods of use thereof. Also described are methods of treating microvascular complications of diabetes by decreasing expression and/or activity of SHP-1.

8 Claims, 9 Drawing Sheets

Mice p=0.25
Mean ± SD

SHP1/2

β-actin control        DM p=0.16
Mean ± SD control    DM

METHODS OF MODULATING METABOLIC MEMORY

CROSS-REFERENCE TO RELATED APPLICATIONS

This application is the U.S. national stage under 35 USC §371 of International Application Number PCT/US2007/075004, filed on Aug. 1, 2007, which claims the benefit under 35 USC §119(e) to U.S. Provisional Patent Application Ser. No. 60/821,119, filed on Aug. 1, 2006, and U.S. Provisional Patent Application Ser. No. 60/945,865, filed on Jun. 22, 2007, the entire contents of which are hereby incorporated by reference.

FEDERALLY SPONSORED RESEARCH OR DEVELOPMENT

This invention was made with Government support under Grant No. R01 EY016150-01A1 awarded by the National Eye Institute of the National Institutes of Health. The Government has certain rights in the invention

TECHNICAL FIELD

This invention relates to methods of identifying modulators of metabolic memory, for the treatment of microvascular complications of diabetes.

BACKGROUND

Diabetic retinopathy (DR), diabetic nephropathy (DN), and other microvascular complications of diabetes are caused by hyperglycemia, although genetic factors play an important role. Intensive glycemic control has been shown to delay the onset or progression of DR and DN in diabetic patients (The Diabetes Control and Complications Trial Research Group, N. Engl. J. Med. 329, 977-86. (1993); UK Prospective Diabetes Study (UKPDS) Group. Lancet 352, 837-53. (1998)). However, once the pathology of DR has been established, clinical studies have shown that it is very difficult to stop or reverse the progression of the vascular pathologies of DR or DN. The Epidemiology of Diabetes Interventions and Complications (EDIC) study, which followed type 1 diabetic patients for over ten years after the Diabetes Control and Complications Trial (DCCT) study ended, showed that prevalence of retinopathy and nephropathy continue to develop at a greater rate in those patients who initially had poor glycemic control. This occurred even after ten years of sharing similar glycemic control between the intensive and standard control groups (The Diabetes Control and Complications Trial/Epidemiology of Diabetes Interventions and Complications Research Group. JAMA 287, 2563-9 (2002); The Diabetes Control and Complications Trial/Epidemiology of Diabetes Interventions and Complications Research Group. JAMA 290, 2159-67 (2003)). Surprisingly, the prevalence of DR and DN continued to diverge between these two groups, hence the phrase, "metabolic memory."

SUMMARY

The present invention is based, in part, on the idea that hyperglycemia activates Src homology 2 domain-containing tyrosine phosphatase 1 (SHP-1) in pericyte and podocyte cells, inducing pathologies in the retinal and renal vessels, which play important roles in DR and DN. Thus, specific inhibitors of SHP-1 can be used as therapeutic agents to reverse the induction of metabolic memory by hyperglycemia in retinal, renal, and possibly other microvascular cells, to delay or ameliorate diabetes microvascular complications. Also described herein are methods for identifying novel treatment for these disorders.

The findings described herein suggest that high glucose (HG, simulating hyperglycemia) can induce persistent cellular changes, i.e., "metabolic memory," which ultimately result in an increased rate of apoptosis in cells such as pericytes. These changes are partially induced by oxidative stress and PKC δ activation to cause p38 MAPK activation, NFκB translocation and the apoptotic cascade, and an increase in SHP-1 levels and activity. Thus, a reversal or amelioration of metabolic memory may be accomplished by reduction of SHP-1 levels or activity, thereby delaying or ameliorating microvascular complications of diabetes, e.g., DR and DN.

Methods of Reversal and Treatment of Microvascular Complications

In another aspect, the invention provides methods for the treatment of disorders associated with metabolic memory, e.g., diabetic retinopathy (DR), diabetic nephropathy (DN), and other microvascular complications of DM. The methods include administering a therapeutically effective amount of an inhibitor of SHP-1, to a subject who is in need thereof. In some embodiments, the inhibitor of SHP-1 is an SHP-1 specific inhibitory nucleic acid, e.g., an antisense, siRNA, ribozymes, and aptamers, or an SHP-1 dominant negative.

Also provided are methods for determining a subject's risk of developing diabetic retinopathy, diabetic nephropathy, or other microvascular complications of diabetes mellitus (DM). The methods include obtaining a sample including cells from the subject; and determining a level of SHP-1 protein or mRNA in the sample. The level of SHP-1 protein or mRNA is indicative of the subject's risk of developing diabetic retinopathy, diabetic nephropathy, or other microvascular complications of DM. In some embodiments, the sample includes cells from the retina, vitreous, or kidney.

In one aspect, the invention provides methods for the treatment of disorders associated with metabolic memory in a subject, e.g., diabetic retinopathy (DR) or diabetic nephropathy (DN). The methods include administering a therapeutically effective amount of an inhibitor of SHP-1, to a subject who is in need thereof.

In some embodiments, the inhibitor of SHP-1 is an SHP-1 specific inhibitory nucleic acid, e.g., an inhibitory nucleic acid selected from the group consisting of an SHP-1 specific antisense, siRNA, ribozymes, aptamers, and a nucleic acid encoding an SHP-1 dominant negative.

In another aspect, the invention provides methods for determining a subject's risk of developing diabetic retinopathy, diabetic nephropathy, or other microvascular complications of diabetes mellitus (DM). The methods include obtaining a sample comprising cells from the subject; and determining a level of SHP-1 protein or mRNA in the sample, wherein the level of SHP-1 protein or mRNA is indicative of the subject's risk of developing diabetic retinopathy, diabetic nephropathy, or other microvascular complications of DM. In some embodiments, the sample comprises cells from the retina, vitreous, or kidney of the subject.

In some embodiments, the methods include comparing the level of SHP-1 in the sample to a predetermined reference level, wherein a level of SHP-1 that is above the reference level indicates that the subject has an increased risk of developing diabetic retinopathy, diabetic nephropathy, or other microvascular complications of DM.

Method of Time Course Assays for Cultured Cells

Also described herein are cell based assays, e.g., using pericytes or podocytes, that can be used as a screen for compounds useful to treat diabetic retinopathy, diabetic nephropathy, and other microvascular complications of diabetes mellitus (DM). The description of the method of time course for cultured cells as described below.

To determine whether PKC action induced by hyperglycemia can be reversed by reestablishment of normoglycemic level, pericytes are grown until 70% confluent and then treated with high glucose (HG; 20 mM) for 24 to 72 hours (h). An in vitro model of the metabolic memory effect is created by stimulation of cells, e.g., pericytes or podocytes, with HG for 72 h and then returned to low glucose (LG; 5.5 mM) for a period of 24 to 72 h. Exemplary treatment groups are as follows:

A) 72 h with LG
B) 24 h with HG
C) 72 h with HG
D) 72 h with HG, then 24 h with LG
E) 72 h with HG, then 72 h with LG Following these time course treatments, apoptosis, PKC activity (in situ assay), cytosolic and membrane localization of PKC isoforms, p38 MAPK phosphorylation, SHP-1 expression, PDGF-13 receptor activation and phosphorylation, and caspase 3/9 activation will be measured, e.g., by standard methods such as immunoblotting or ELISA.

Thus in one aspect, the invention provides methods for identifying candidate compounds for treating or preventing diabetic retinopathy, diabetic nephropathy, or other microvascular complications of diabetes mellitus (DM). The methods include the steps of:

(a) culturing a population of cells in the presence of media with normal glucose (NG, about 5.5 mM glucose) until the cells are about 60-80% confluent, e.g., about 70% confluent;

(b) then culturing the cells in the presence of high glucose media (HG; about 20 mM glucose) for 24 to 72 hours, e.g., for 72 hours;

(c) then culturing the cells in the presence of normal glucose media (NG; about 5.5 mM glucose, also referred to herein as low glucose or LG) for a period of 24 to 72 hours;

(d) adding a test compound during one or more of steps (a), (b), and/or (c), and (e) evaluating one or more of: apoptosis, levels or activity of SHP-1, levels of protein kinase C (PKC) activity, levels of cytosolic and membrane fraction of PKC isoforms, levels of p38 MAPK phosphorylation, and levels of caspase 3/9 activation, in the cells, in the presence and absence of the test compound.

A test compound that has at least one effect selected from the group consisting of decreasing apoptosis, decreasing levels of PKC activity, decreasing membrane translocation, decreasing p38 MAPK phosphorylation, and decreased caspase activation, is a candidate compound for treating or preventing diabetic retinopathy and other microvascular complications of DM.

In some embodiments, the level of SHP-1, PKC activity, cytosolic and membrane fraction of PKC isoforms, p38 MAPK phosphorylation, or caspase 3/9 activation is measured by immunoblotting or enzyme-linked immunosorbent assay (ELISA).

In some embodiments, the level of apoptosis is measured by DNA fragmentation.

In some embodiments, the cells are grown in a multiwell plate, e.g., 48 or 96 well plate.

In some embodiments, the cells are pericytes, podocytes, or mesangial cells.

In some embodiments, the cells have been passaged (e.g., split) fewer than five times.

In some embodiments, the test compound is a PKC isoform-specific inhibitor, e.g., a specific inhibitor of PKC delta. In some embodiments, the test compound is a specific inhibitor of MAPK alpha or beta.

In some embodiments, the test compound is a specific inhibitor of SHP-1.

In some embodiments, the methods further include administering a candidate compound to an animal model of diabetic retinopathy or other microvascular complications of DM, and evaluating an effect of the candidate compound on a clinical parameter of the model, wherein a candidate compound that has a desirable effect on the clinical parameter is a candidate therapeutic agent for the treatment of diabetic retinopathy and other microvascular complications of DM.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety, including the priority applications, U.S. Ser. No. 60/821,119, filed Aug. 1, 2006, and U.S. Ser. No. 60/945,865, filed Jun. 22, 2007. In case of conflict, the present specification, including definitions, will control.

DETAILED DESCRIPTION

Figure 1:
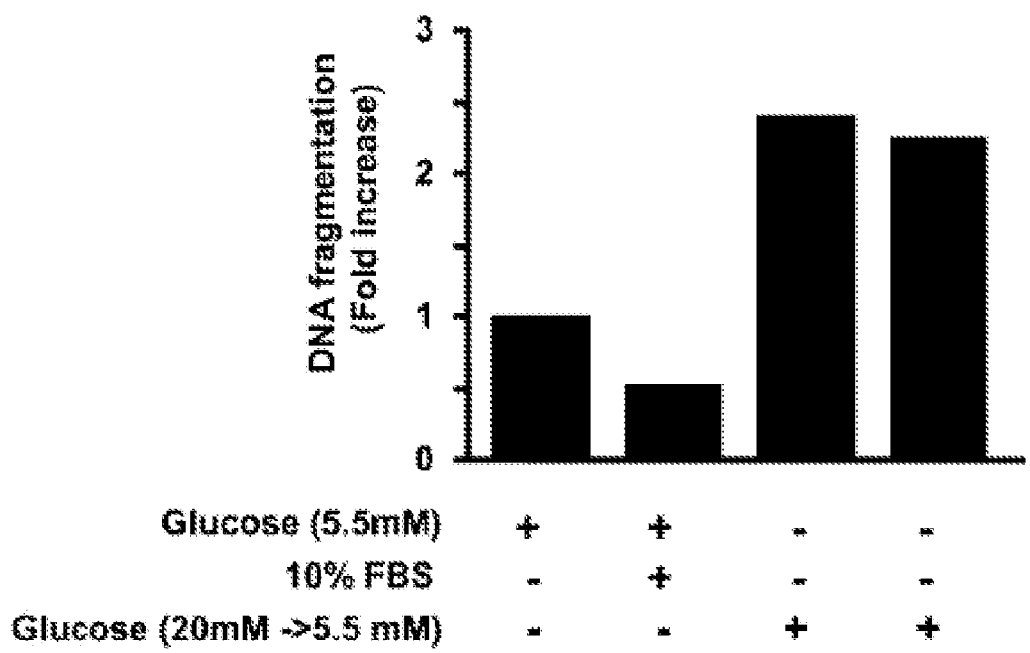
FIG. 1 is a bar graph showing the effects of high levels of D-glucose on pericyte DNA fragmentation (a measure of apoptosis).

Pericyte apoptosis is an early specific pathology of DR. Hyperglycemia-induced apoptosis in retinal pericytes in our studies revealed that PKC δ activation involved p38 MAPK and oxidative stress, and PKC δ remained activated even after the reduction of glucose to normal physiological levels of 5.6 mM (low glucose, LG). These data suggest that activation of PKC δ and p38 MAPK α/β isoforms may play a role in "metabolic memory" and pericyte loss in diabetic retinopathy (DR) and podocyte loss in diabetic nephropathy (DN). Further characterization of HG treatment revealed that PDGF-BB was prevented from inducing tyrosine phosphorylation of the PDGF-β receptor; subsequently the ERK and AKT cell survival pathways were not activated. The expression of SHP-1, a protein tyrosine phosphatase (PTP), was increased by HG levels. SHP-1 "can block PDGF-β receptor phosphorylation by PDGF-BB," and the results indicate that SHP-1 agonists will reverse the effects of HG treatment, reverse metabolic memory, and thus lessen diabetic retinopathy.

Surprisingly, HG-induced expression of SHP-1, abrogation of PDGF-BB actions and apoptosis were prevented by the expression of a dominant-negative mutant of p38α MAPK using adenoviral vectors or by co-treatment with a p38 MAPK inhibitor (SB203580). Importantly, these inhibitors of p38 MAPK also reversed apoptosis in the pericytes when they were added during LG conditions after HG exposure. These results indicate that PKCδ isoform induced activation of p38 MAPK and expression of SHP-1 plays a critical role in affecting the cell survival signaling pathway, affects metabolic memory and apoptosis in pericytes, and leads to DR. Similar results were seen in podocytes and glomeruli, indicating that similar pathophysiological processes underlie DN.

Metabolic Memory

The classic report by Engerman and Kern showed that good glycemic control prevented the development of pericyte loss and acellular capillaries in diabetic dogs after five years of diabetes (Engerman & Kern, Diabetes 36, 808-12 (1987)). Interestingly, diabetic dogs that experienced poor glycemic control for the first 2.5 years and then managed to maintain good glycemic control for the next 2.5 years continued to manifest pericyte ghosts or apoptosis, microaneurysms and acellular capillaries. These findings suggest there is "metabolic memory" in retinal capillaries, especially in the pericytes. These findings of progressing capillary pathologies in diabetes even after the removal of hyperglycemia have also been reported in rodent models of diabetes (Kowluru et al., Acta Diabetol 41, 194-9 (2004)). At this time, the mechanisms underlying this "metabolic memory" is unknown, although increases in oxidative stress and AGE's have been implicated as initiating factors in rodent models of diabetic retinopathy (Brownlee, Nature 414, 813-20. (2001); Barile et al., Invest Opthalmol V is Sci 46, 2916-24 (2005)). Multiple mechanisms have been proposed to date. Multiple agents, such as antioxidants, anti-glycation compounds, inhibitors of aldose reductase and anti-inflammatory drugs have been reported to delay the onset of retinal vascular changes in diabetic animals (Sheetz, Jama 288, 2579-88 (2002)). However, most clinical trials using these agents have not been able to reproduce the positive findings observed in animal models of diabetes for retinopathy, nephropathy or neuropathy (He and King, in International Textbook of Diabetes Mellitus. (ed. R. A. De Fronzo, E. F., Harry Keen and Paul Zimmet) p1135-1159 (John Wiley & Sons., 2004)).

In the experiments described herein, various potential mechanisms for the "metabolic memory" in the pericytes after their exposure to HG were explored. PKC activation was measured and found to have the same pattern as the time course as the effects of HG on apoptosis and DNA synthesis. The delayed effects of HG on PKC activation in the pericytes mirrored its actions in retinal endothelial cells (REC) (Shiba et al., Am J Physiol 265, E783-93 (1993)). In addition to PKC activation, the effect of HG on p38 MAPK activation was also characterized, since PKC δ activation induced by HG can activate p38 MAPK in aortic smooth muscle and renal mesangial cells. Further, p38 MAPK activation has been shown to initiate a complex process leading to apoptosis (Kyriakis et al., Physiol Rev 81, 807-69 (2001)).

As shown herein, HG increased phosphorylation of p38 MAPK by 2-fold in pericytes after three days of exposure, in parallel with PKC δ activation and increases in apoptosis; no effects on JNK were observed. The effect of HG on ERK 1/2 (MAPK) phosphorylation was also evaluated. HG inhibited ERK 1/2 phosphorylation induced by serum and growth factors after three days of exposure. Addition of anti-oxidant, n-acetylcysteine and an inhibitor of p38 MAPK α and β were partly able to prevent the apoptotic effects of HG A PKC β specific inhibitor, RBX, was ineffective to prevent HG induced p38 MAPK activation or apoptosis.

In summary, these findings suggest HG can induce persistent cellular changes, referred to herein as metabolic memory, which ultimately result in an increased rate of apoptosis in pericytes and podocytes. These changes are partially induced by oxidative stress and PKC δ activation to cause p38 MAPK activation, NFκB translocation and the apoptotic cascade.

Src Homology 2 (SH2)-Containing Protein Phosphatase 1 (SHP-1)

Src homology 2 (SH2)-containing protein phosphatase 1 is a protein of about 66-70 kDa that is predominantly expressed in hematopoietic and epithelial cells. In general, the protein is found localized in the cytoplasmic or nucleus. In general, protein tyrosine phosphatases (PTP) catalyze the dephosphorylation of phosphotyrosine peptides, and regulate phosphotyrosine levels in signal transduction pathways. SHP-1 negatively regulates growth-promoting receptors or their targets (as compared to SHP-2 which plays a positive role in cell signaling (e.g., via PDGFR and FGFR)). SHP-1 is believed to dephosphorylate the PDGF receptor and the p85 subunit of PI3K. See, e.g., Yu et al., J. Biol. Chem., 273(6):3687-3694, 1998.

Figure 13:
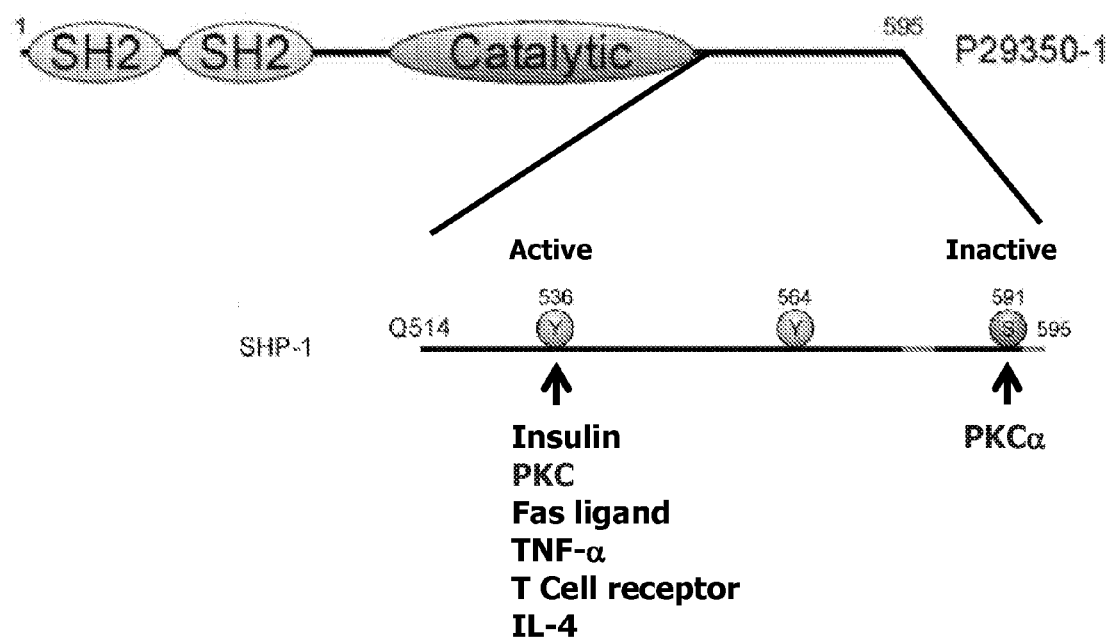
FIG. 13 is a diagram of the SHP-1 protein.

SHP-1 is also known as protein-tyrosine phosphatase, non-receptor-type, 6 (PTPN6); protein-tyrosine phosphatase 1c (PTP1C); tyrosine phosphatase SHP-1; and hematopoietic cell phosphatase (HCPH). The N-terminal part of SHP-1 contains two tandem Src homolog (SH2) domains, which act as protein phospho-tyrosine binding domains, and mediate interactions with its substrates. A schematic diagram of the SHP-1 protein is shown in FIG. 13.

There are two splice variants of the human SHP-1:
Protein Tyrosine Phosphatase, Non-Receptor Type 6 Isoform 1

Genbank Acc. Nos. NM_002831.4 (nucleic acid); NP_002822.2 (amino acid)

Variant 1 is the longer transcript, but encodes the shorter protein (isoform 2).

Conserved Domains:

Location: 4-99 and 110-213: SH2; Src homology 2 domains (Signal transduction, involved in recognition of phosphorylated tyrosine (pTyr)).

Location: 243-517 or 272-514: PTPc; Protein tyrosine phosphatase, catalytic domain Protein Tyrosine Phosphatase, Non-Receptor Type 6 Isoform 2

Genbank Acc. Nos. NM_080548.3 (nucleic acid); NP_536858.1 (amino acid)

Variant 2 uses a different segment for its 5' UTR and 5' coding region, when compared to variant 1. The encoded protein (isoform 2) has a longer and distinct N-terminus, as compared to isoform 1.

Conserved Domains:

Location: 5-101 and 112-215: SH2

Location: 274-516 or 245-519: PTPc

SHP-1 Dominant Negatives

SHP-1 dominant negative polypeptides are known in the art. For example, a single amino acid substitution in the active site of SHP-1 (C453S, using the numbering of isoform 1) ablates phosphatase activity. This enzymatically incative form of SHP-1 cannot dephosphorylate ITIM sequences and binds to ITIM sequences for significantly longer periods of time, preventing the endogenous phosphatase from inhibiting signal transduction. Therefore, it is likely that this mutation functions as an efficient dominant-negative mutation. See, e.g., Dustin et al., J. Immunol., 162: 2717-2724, 1999. Use of this SHP-1 dominant negative is also reported at Dubois et al., Nat. Med. 12(5): 549-556 (2006).

Dominant negative mutants of SHP-1 comprising just the two SH2 domains have also been constructed, see, e.g., Berchtold et al., Mol. Endocrinol., 12(4):556-567 (1998).

Methods of Screening

The invention includes methods for screening of test compounds, to identify compounds that modulate activity or expression of SHP-1, for use in the treatment, delay, or prevention of onset or progression of diabetic retinopathy (DR) or diabetic nephropathy (DN), or other microvascular complications of DM.

The methods described herein can be used to identify compounds that bind to SHP-1. In addition, the effect of a test compound on SHP-1 activity, e.g., on SHP-1 phosphatase activity, can be determined For example, the methods can be used to identify compounds that demonstrate binding to SHP-1 mRNA or protein.

Thus, in general, the methods will include providing a sample that includes

SHP-1, e.g., a purified SHP-1 sample or a cell expressing SHP-1.

Screening methods suitable for use in these embodiments are known in the art and include, but are not limited to, yeast or mammalian 2-hybrid systems, tagged protein assays, immunoprecipitation assays, and proteomics assays. These methods can be used to identify natural (i.e., endogenous) regulators of SHP-1, for example.

In some embodiments, the methods include identifying compounds that affect levels or activity of SHP-1, and then determining the effect of those compounds on phosphorylation of PDGFβ-R by PDGF-BB; in this case, the sample can include a cell expressing SHP-1, PDGFβ-R, and PDGF-BB, with or without p38 MAPK alpha. In order to evaluate the ability of a compound to affect metabolic memory, it will generally be desirable to test the compound in a cell. For example, the methods can include adding the compound to cells that express all of these proteins (SHP-1, PDGFβ-R, and PDGF-BB, and p38 MAPK alpha), and exhibit metabolic memory. The methods can then include selecting a compound identified as decreasing SHP-1 activity or levels, contacting the cells with the compound, and evaluating an effect of the compound on metabolic memory (e.g., using an assay described herein). In some embodiments, the methods further include determining whether the compound has an effect on phosphorylation of, for example, PDGFβ-R, and selecting a test compound If it selectively inhibits the SHP-1 block of PDGFβ-R phosphorylation by PDGF-BB.

In some embodiments, the methods will include determining whether a compound has an effect on an in vitro model, e.g., apoptosis in a cellular model of metabolic memory as described herein, or an in vivo model, e.g., retinopathy or nephropathy in a diabetic animal model. A number of useful animal models of diabetes are known in the art, e.g., those described herein and in Breyer et al., J. Am. Soc. Nephrol. 16:27-45 (2005). The following include some exemplary assays for use in vitro or in vivo.

DNA Fragmentation (A Measure of Apoptosis)

Cell apoptosis will be evaluated by measurement of DNA fragmentation using cell death detection kit (ROCHE diagnostics). Approximately 15000 cells are seeded in 96-well plates in DMEM with 20% FBS for 18 hours. BRP are starved for 24 hours and then stimulated with either 5.5 or 20 mM of d-glucose for an addition 72 hours. DNA fragmentation is measured in accordance to manufacture's protocol. Increases in caspase 3+9 cleared will also be measured using immunoblot analysis. Measurement of NF-κB activity in cultured cells. Activity of NF-κB will be assessed by a microwell colorimetric assay using the TransAM NFκB transcription factor assay kit (Active Motif, Carlsbad, Calif.) following manufacturer's instruction (Renard et al., Nucleic Acids Res 29, E21 (2001)).

Retinal Blood Flow

Video fluorescein angiography is employed to determine retinal blood flow. The video fluorescein angiography system has been previously described. Briefly, the system consists of a Nikon fundus camera coupled to a low light-level SIT camera. The NTSC output signal is digitized by a Targa 2000 frame grabber from Truevision (Indianapolis, Ind.). The images are digitized at a rate of 30 frames/second with a resolution of 640×480×8 pixels. The angiogram sequence is stored as a sequential series of TIF images. Analysis of the digitized angiograms is performed on a frame-by-frame basis using in-house proprietary software.

The procedure to measure retinal blood flow has been previously described. Animals undergo surgical implantation of a polyvinyl catheter into the right jugular vein. After 24 hours, the animals are anesthetized by intraperitoneal injection of sodium pentobarbital (50 mg/kg) and the catheter exposed. The left eye is dilated with 1% tropicamide. Angiograms are obtained by rapidly injecting 5 μl of 10% sodium fluorescein. Analyses of the digitized angiograms are performed using an in-house quantifying software. Dye dilution curves of the dynamic fluorescein intensities are obtained from the primary arteries and veins at a distance of 1.5 optic disc diameters. The dye dilution curves are fit by a log-normal distribution function and the curve-fit parameters used to determine the mean arterial and venous circulation times. The mean circulation time is defined as the difference between the mean venous and arterial filling times. The diameter of the primary vessels is measured at the defined sample sites by a boundary-crossing algorithm. Segmental retinal blood flow is calculated by the sum of the squares of the retinal artery and vein diameters divided by the mean circulation time.

Typical variances for retinal blood flow measurements indicate that we will need 7 to 8 animals per test group to demonstrate a 25-30% change in RBF with a statistical significance of 0.05 at a power of 0.8 using unpaired Student's t-test or ANOVA.

Retinal Permeability Measurements Using the Evans-Blue Dye Technique

Twenty-four hours prior to the experiment, animals were anesthetized using Sodium Nembutol at 50 mg/kg (Abbott Laboratories, North Chicago, Ill.) and a 1 mm polyvinyl catheter (Braintree Scientific, Braintree, Mass.) was inserted into the right jugular vein. The distal end of the catheter was positioned subcutaneously for later access. On the day of the experiment, the animals were weighed and the dose of Evans-Blue dye (Sigma-Aldrich, St. Louis, Mo.) calculated. Animals were anesthetized, the catheter was exposed, and Evans-Blue dye was injected (45 mg/kg). The dye was allowed to circulate for 2 hours. Additional anesthesia was given at the end of 2 hours when a laparotomy was performed to expose the descending vena cava. 0.9 cc of heparinized venous blood was withdrawn to measure average plasma dye concentration. The chest cavity was exposed and a 25 gauge butterfly was inserted into the left ventricle. The arch of the vena cava was cut and 30 cc of saline infused into the heart at physiological pressure through a butterfly catheter. After the saline infusion, 30 cc of 10% Formalin was infused to fix the tissues. Following tissue fixation, the eyes were enucleated. The retina from each eye was placed in a pre-weighed eppendorf tube. Retinal samples were placed in a dry vacuum for 5 hours after which time dry weight of each retina was measured. The dried retinas were incubated in formamide (Sigma-Aldrich) overnight at 72° C. to extract the Evans-Blue dye. Following incubation, the resulting extract was ultra-centrifuged at 30,000×g for 30 minutes and the supernatent used for spectrophotometric measurements. Absorbance was measured at 620 nm (Evans-blue maximum) and 740 nm (Evans-Blue minimum).

Electroretinography

A contact lens electrode with a built-in light-emitting diode (LED) was used for a stimulus. This LED has a relatively broad asymmetrical spectral bandwidth with two peaks at approximately 430 and 540 nm. The stimulus duration, stimulus intensity, and background intensity were controlled by the LED-driver (WLS-20, Mayo Co., Nagoya, Japan). Maximal stimulus was $1.4 \times 10^4$ cd/m$^2$ at the cornea. A white diffuser is placed between the LED and cornea to produce a homogenous ganzfeld stimulus and background illumination to the retina. [Miyake, Horiguchi] The eyes were fully dark-adapted for at least 60 min and the following procedures were performed under dim red light. The animals were anesthetized with intramuscularly injection of 50 mg/kg ketamine hydrochloride (Ben Venue Laboratories, Bedford, Ohio) and xylazine hydrochloride (Sigma, St. Louis, Mo.). The pupils were dilated with 1% tropicamide (Mydriacyl: Alcon, Fort Worth, Tex.). The animals were placed on a heating pad to maintain the body temperature at 37° C. Needle electrodes were inserted subcutaneously in the forehead and the tail which served as the reference and ground electrodes, respectively. A drop of Gonosol was placed on the cornea to maintain an electrolytic contact between the LED electrode and the surface of the cornea. ERG's were obtained with a stimulus intensity of $1.4 \times 10^4$ cd/m$^2$ at duration of 5 milliseconds. The signals were amplified with a bandpass filter between 1 and 1000 Hz (PowerLab ML750, ADInstruments, Sydney, Australia) Three signals were recorded at an interval of 60 seconds and averaged. Resulting spectra were analyzed for peak latencies and signal amplitude for the a-wave, b-wave, and oscillatory potentials 1 through 4.

Glomerular Filtration Rate (GFR)

Inulin clearance, the traditional gold-standard measurement, has also been adapted for use in mice. Clearance of FITC-labeled inulin has been measured in both anesthetized and conscious mice (Qi et al., Am. J. Physiol. Renal. Physiol. 286: F590-F596 (2004); Lorenz and Gruenstein, Am. J. Physiol. (Lond.) 276: F172F177, (1999)). Serial measurements of inulin clearance can be determined in conscious mice over a period of months using an intravenous bolus FITC inulin and measuring the decay rate of inulin in plasma (Qi et al., supra).

Blood Pressure (BP)

There are several proven methods for monitoring BP in mice that can be used in the methods described herein. Indirect measurements using tail-cuff manometry systems are simple and noninvasive. Intra-arterial pressure can also be measured directly, e.g., in conscious mice, by cannulating arteries with catheters tunneled under the skin, exteriorized, and connected to an external transducer and/or monitor, e.g., a radiotelemetry unit.

Proteinuria/Albuminuria

Albuminuria determined by an immunoassay generally provides a reliable assessment of proteinuria.

Test Compounds

In some embodiments, the test compounds are initially members of a library, e.g., an inorganic or organic chemical library, peptide library, oligonucleotide library, or mixed-molecule library. In some embodiments, the methods include screening small molecules, e.g., natural products or members of a combinatorial chemistry library. These methods can also be used, for example, to screen a library of proteins or fragments thereof, e.g., proteins that are expressed in liver or pancreatic cells.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art, e.g., methods for synthesizing libraries of small molecules, e.g., as exemplified by Obrecht and Villalgordo, *Solid-Supported Combinatorial and Parallel Synthesis of Small-Molecular-Weight Compound Libraries*, Pergamon-Elsevier Science Limited (1998). Such methods include the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of libraries, including small molecule libraries, are commercially available.

In some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, β-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). In some embodiments, the test compounds are nucleic acids, e.g., DNA or RNA oligonucleotides.

In some embodiments, test compounds and libraries thereof can be obtained by systematically altering the structure of a first test compound. Taking a small molecule as an example, e.g., a first small molecule is selected that is, e.g., structurally similar to a known phosphorylation or protein recognition site. For example, in one embodiment, a general library of small molecules is screened, e.g., using the methods described herein, to select a fist test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

In some embodiments, test compounds identified as "hits" in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in treating disorders described herein. Thus, the invention also includes compounds identified as "hits" by a method described herein, and methods for their administration and use in the treatment, prevention, or delay of development or progression of a disease described herein.

Pharmaceutical Compositions

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Treatment

The methods described herein include methods for the treatment of disorders associated with metabolic memory, i.e., DR or DN. In some embodiments, the disorder is DR. Generally, the methods include administering a therapeutically effective amount of an inhibitor of SHP-1, to a subject who is in need of, or who has been determined to be in need of, such treatment. Inhibitors of SHP-1 include SHP-1 specific inhibitory nucleic acids and dominant negatives, as well as other inhibitors identified by a method described herein.

As used in this context, to "treat" means to ameliorate at least one symptom of the disorder associated with metabolic memory, or to delay or prevent development of the disorder. Preventing development need not be 100%, i.e., preventing development need not happen in all subjects. Often, DR results in a loss of visual acuity due to pericyte apoptosis and microvascular aneurysms; thus, a treatment can result in a reduction in these complications and a return or approach to normal vision. Preferably, the treatment is administered before these complications occur, or before they become severe, to prevent or reduce the loss of visual acuity. DN often results in a reduction in kidney function, associated with glomerular thickening and nodular glomerulosclerosis; a treatment can reduce or prevent the loss of kidney function, and is preferably administered before these complications occur. Administration of a therapeutically effective amount of a composition described herein for the treatment of a condition associated with metabolic memory will result in decreased SHP-1 levels and/or activity, and this relieve the metabolic memory.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present.

Moreover, treatment of a subject with a therapeutically effective amount of the compositions described herein can include a single treatment or a series of treatments.

Methods of Diagnosis

Included herein are methods for determining whether a subject is at risk of developing diabetic retinopathy (DR) or diabetic nephropathy (DN). The methods include obtaining a sample from a subject, and evaluating the presence and/or level of SHP-1 in the sample, and comparing the presence and/or level with one or more references, e.g., a control reference that represents a normal level of SHP-1, e.g., a level in an unaffected subject, and/or a disease reference that represents a level of SHP-1 associated with the presence or increased risk of developing DR or DN. The presence and/or level of a protein can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of SHP-1.

In some embodiments, the presence and/or level of SHP-1 is comparable to the presence and/or level of the protein(s) in the disease reference, and the subject has one or more symptoms associated with SHP-1, or the subject has diabetes, then the subject has DR or DN or has an increased risk of developing DR or DN. In some embodiments, the subject has no overt signs or symptoms of DR or DN, but the presence and/or level of one or more of the proteins evaluated is comparable to the presence and/or level of the protein(s) in the disease reference, then the subject has an increased risk of developing DR or DN. In some embodiments, the sample includes a biological fluid, e.g., blood, semen, urine, and/or cerebrospinal fluid. In some embodiments, once it has been determined that a person has DR or DN, or has an increased risk of developing DR or DN, then a treatment, e.g., as known in the art or described herein, can be administered.

Inhibitory Nucleic Acid Molecules

In some embodiments, the methods described herein can include administering inhibitory nucleic acid molecules that are targeted to a SHP-1 RNA, e.g., SHP-1 specific antisense, siRNA, ribozymes, and aptamers.

siRNA Molecules

RNAi is a process whereby double-stranded RNA (dsRNA, also referred to herein as si RNAs or ds siRNAs, for double-stranded small interfering RNAs) induces the sequence-specific degradation of homologous mRNA in animals and plant cells (Hutvagner and Zamore, Curr. Opin. Genet. Dev.: 12, 225-232 (2002); Sharp, Genes Dev., 15:485-490 (2001)). In mammalian cells, RNAi can be triggered by 21-nucleotide (nt) duplexes of small interfering RNA (siRNA) (Chiu et al., Mol. Cell. 10:549-561 (2002); Elbashir et al., Nature 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell. 9:1327-1333 (2002); Paddison et al., Genes Dev. 16:948-958 (2002); Lee et al., Nature Biotechnol. 20:500-505 (2002); Paul et al., Nature Biotechnol. 20:505-508 (2002); Tuschl, T., Nature Biotechnol. 20:440-448 (2002); Yu et al., Proc. Natl. Acad. Sci. USA 99(9):6047-6052 (2002); McManus et al., RNA 8:842-850 (2002); Sui et al., Proc. Natl. Acad. Sci. USA 99(6):5515-5520 (2002)).

The nucleic acid molecules or constructs can include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed be in vitro from a DNA template, or in vivo from, e.g., shRNA. The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors.

siRNAs can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into the cells with a vector expression T7 RNA polymerase (Jacque (2002), supra).

Antisense

An "antisense" nucleic acid can include a nucleotide sequence that is complementary to a "sense" nucleic acid encoding a protein, e.g., complementary to the coding strand of a double-stranded cDNA molecule or complementary to a SHP-1 mRNA sequence. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence (e.g., the 5' and 3' untranslated regions).

An antisense nucleic acid can be designed such that it is complementary to the entire coding region of a target mRNA, but can also be an oligonucleotide that is antisense to only a portion of the coding or noncoding region of the target mRNA.

For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

In some embodiments, the antisense nucleic acid molecule is an α-anomeric nucleic acid molecule. An α-anomeric nucleic acid molecule forms specific double-stranded hybrids with complementary RNA in which, contrary to the usual 13-units, the strands run parallel to each other (Gaultier et al., Nucleic Acids. Res. 15:6625-6641 (1987)). The antisense nucleic acid molecule can also comprise a 2'-o-methylribonucleotide (Inoue et al. Nucleic Acids Res. 15:6131-6148 (1987)) or a chimeric RNA-DNA analogue (Inoue et al. FEBS Lett., 215:327-330 (1987)).

In some embodiments, the antisense nucleic acid is a morpholino oligonucleotide (see, e.g., Heasman, Dev. Biol. 243: 209-14 (2002); Iversen, Curr. Opin. Mol. Ther. 3:235-8 (2001); Summerton, Biochim. Biophys. Acta. 1489:141-58 (1999).

Target gene expression can be inhibited by targeting nucleotide sequences complementary to a regulatory region (e.g., promoters and/or enhancers) to form triple helical structures that prevent transcription of the SptS gene in target cells. See generally, Helene, C. *Anticancer Drug Des.* 6:569-84 (1991); Helene, C. *Ann. N.Y.* Acad. Sci. 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for a target nucleic acid can include one or more sequences complementary to the nucleotide sequence of a cDNA described herein, and a sequence having known catalytic sequence responsible for mRNA cleavage (see U.S. Pat. No. 5,093,246 or Haselhoff and Gerlach Nature 334:585-591 (1988)). For example, a derivative of a Tetrahymena L-19 IVS RNA can be constructed in which the nucleotide sequence of the active site is complementary to the nucleotide sequence to be cleaved in a target mRNA. See, e.g., Cech et al. U.S. Pat. No. 4,987,071; and Cech et al. U.S. Pat. No. 5,116,742. Alternatively, a target mRNA can be used to select a catalytic RNA having a specific ribonuclease activity from a pool of RNA molecules. See, e.g., Bartel and Szostak, Science 261:1411-1418 (1993).

Aptamers

Aptamers are short oligonucleotide sequences which can specifically bind specific proteins. It has been demonstrated that different aptameric sequences can bind specifically to different proteins, for example, the sequence GGNNGG where N=guanosine (G), cytosine (C), adenosine (A) or thymidine (T) binds specifically to thrombin (Bock et al (1992) Nature 355: 564 566 and U.S. Pat. No. 5,582,981 (1996) Toole et al). Methods for selection and preparation of such RNA aptamers are knotn in the art (see, e.g., Famulok, Curr. Opin. Struct. Biol. 9:324 (1999); Herman and Patel, J. Science 287:820-825 (2000)); Kelly et al., J. Mol. Biol. 256:417 (1996); and Feigon et al., Chem. Biol. 3: 611 (1996)).

Administration of Inhibitory Nucleic Acid Molecules

The inhibitory nucleic acid molecules described herein can be administered to a subject (e.g., by direct injection at a tissue site), or generated in situ such that they hybridize with or bind to cellular mRNA and/or genomic DNA encoding a target protein to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid nucleic acid molecules to peptides or antibodies that bind to cell surface receptors or antigens. The inhibitory nucleic acid nucleic acid molecules can also be delivered to cells using the vectors described herein. To achieve sufficient intracellular concentrations of the inhibitory nucleic acid molecules, vector constructs in which the inhibitory nucleic acid nucleic acid molecule is placed under the control of a strong promoter can be used.

EXAMPLES

The invention is further described in the following examples, which do not limit the scope of the invention described in the claims.

Example 1

Activation of PKCdelta and p38 MAPK in a Cultured Cell Model of Metabolic Memory Various potential mechanisms for the metabolic memory process in retinal pericytes were explored in vitro. Cells were culture in high glucose (HG, 20 mM glucose) for about 72 hours, and then for another 24 hours in low glucose (LG, 5.6 mM glucose). This mimics a period of hyperglycemia followed by normoglycemia, a common pattern in diabetics, who often have a period of poorly controlled glycemia before finding a regime that provides better control, thus providing a cultured cell model of metabolic memory.

Exposure of cultured bovine retinal pericytes to HG for three to five days increased apoptosis in pericytes (an early specific pathology for DR) by 221% (P<0.05) (FIG. 1). Interestingly, apoptosis in the pericytes did not decrease when the glucose levels were reduced to 5.5 mM (low glucose, LG) after an initial exposure of three to five days to HG conditions (FIG. 1). This correlates well with the observation that a period of poor glycemic control, even if followed by excellent control, increases a diabetic's likelihood of developing a microvascular complication of diabetes, e.g., DN or DR.

PKC activation was also measured using a standard assay, and had the same pattern as the time course as the effects of HG on pericyte apoptosis and DNA synthesis. The delayed effects of HG on PKC activation in the pericytes mirrored its actions in retinal endothelial cells (REC).

Figure 2:
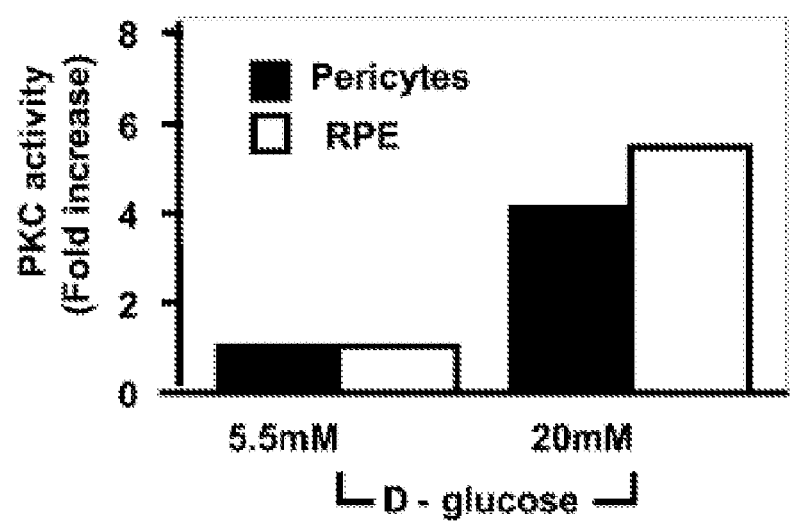
FIG. 2 is a bar graph showing the effects of high glucose on PKC activity in pericytes (filled bars) and RPE (open bars).
Figure 3:
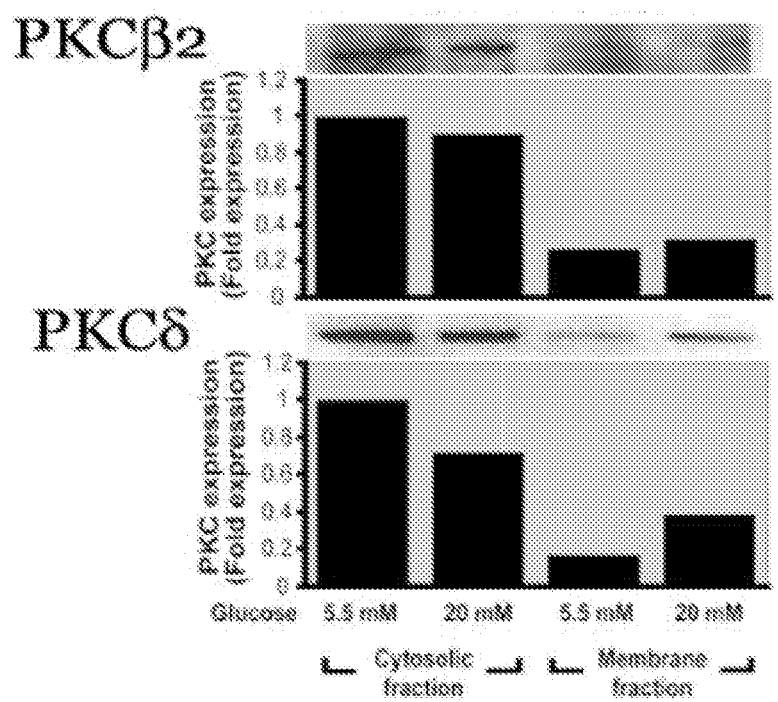
FIG. 3 is a pair of Western blots with quantitative bar graphs showing the effects of high glucose on membranous and cytosolic expression levels of PKCβ (top panel) and PKCδ in pericytes.

Previous studies have shown that pericytes contain PKC isoforms α, β1, β2, δ and ε. Incubating pericytes and retinal pigment epithelial cells (RPE) with 20 mM of glucose (HG) increased PKC activity by 3-4 folds as compared with cells cultured in 5.6 mM (LG) (FIG. 2). In pericytes, HG increased mainly PKC δ isoform translocation, not δ1/2, (FIG. 3) a different pattern from retinal endothelial cells (REC) where predominantly β1/2 was activated. Using the same pericyte cell culture model, incubation of cells with HG for three days as compared with LG in 1% fetal bovine serum induced significant increases in markers of apoptosis as measured by DNA fragmentation (FIG. 1).

Figure 4:
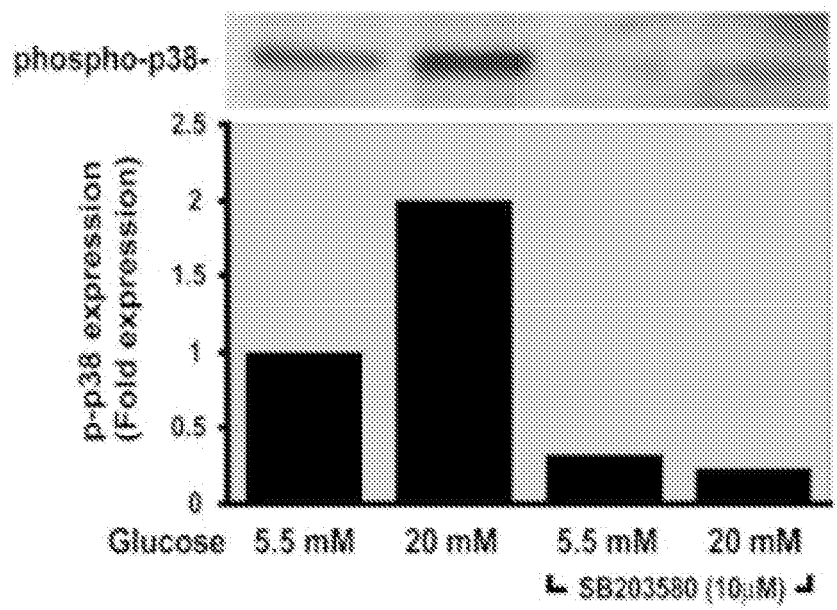
FIG. 4 is a Western blot and bar graph showing the effects of low and high glucose levels on p38 MAPK activation in bovine pericytes.

In addition to PKC activation, the effect of HG on p38 MAPK activation was also characterized, since PKC δ activation induced by HG can activate p38 MAPK in aortic smooth muscle and renal mesangial cells. Further, p38 MAPK activation has been shown to initiate a complex process leading to apoptosis. HG was able to increase the phosphorylation of p38 MAPK by 2-fold in pericytes after three days of exposure (FIG. 4) in parallel with PKC δ activation and increases in apoptosis; no effects on JNK were observed.

The role of p38 MAPK was studied further using SB203580, a specific inhibitor for p38 MAPK a and 0 and adenoviral vector of dominant negative p38 MAPKα and β isoforms (Wang et al., J Biol Chem 273, 2161-8 (1998)), either at the same time as starting HG condition or after 3 days of HG when cells are returning to LG condition. In addition, the effects of the antioxidant N-acetylcysteine (NAC) were also evaluated. Activation of p38 MAPK β and δ was evaluated by immunoblotting with anti-phospho p38 MAPK α and δ antibodies. The results, shown in FIG. 14, indicate that treatment with NAC and SB203580 was partly able to prevent the apoptotic effects of HG, but not totally effective in reversing the inhibitory effects of HG once they have been established.

In summary, HG increases PKC δ activation, p38 MAPK α and β phosphorylation and apoptosis, as measured by DNA fragmentation. Thus, these findings suggest HG can induce persistent cellular changes, i.e., "metabolic memory," which ultimately result in an increased rate of apoptosis in cells such as pericytes.

Example 2

High Glucose Treatment of Pericytes Increased Expression of the Protein Tyrosine Phosphatase SHP-1

It has been postulated that the increased rate of pericyte loss or apoptosis may be associated with abnormalities in platelet-derived growth factor (PDGF) activity, since PDGF-3 receptor knockout mice lacked pericytes and die in utero. However, the mechanisms by which hyperglycemia inhibits PDGF action on pericytes are not known; contradictorily, PDGF-β mRNA expression appears to be increased in the retina of diabetic rats. HG conditions prevented PDGF-BB-induced tyrosine phosphorylation of PDGF-β receptor and subsequently inhibited the activation of the ERK and AKT signaling pathways, which are related to cell survival.

Protein tyrosine phosphatases (PTPs) play a key role in the regulation of receptor tyrosine kinases such as the PDGF-β receptor. Thus, experiments were performed to determine the pathway by which glycemic memory prevented tyrosine phosphorylation of the PDGF-Beta receptor. Cultured pericytes were exposed to either low glucose conditions (~5.5 mM glucose, LG), high glucose conditions (~20 mM glucose, HG), or high glucose followed by low glucose (~20 mM, ±5.5 mM glucose, HG+LG) for 72 hours per exposure. Pericytes were lysed, and lysates were run on an SDS/PAGE gel, then transferred to nitrocellulose for immunoblotting, according to already published procedures. Commercially available antibodies for SHP-1 and another protein tyrosine phosphatase, PTP-1B were used to probe the blot, according to manufacturer's instructions.

Figure 5A:
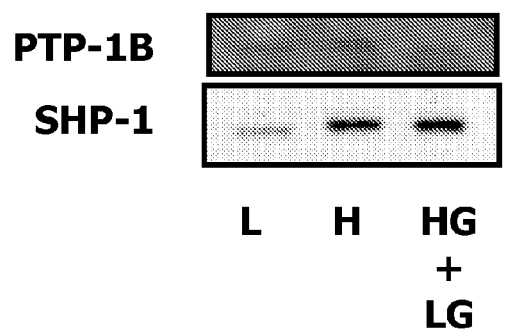
FIG. 5A is a Western blot showing levels of PTP-1B and SHP-1 in pericytes incubated in LG, HG, and HG then LG (metabolic memory) conditions, showing a persistent increase in SHP-1 that remains even after the cells are returned to LG

The expression of protein tyrosine phosphatase SHP-1 in pericytes was increased under high glucose conditions, and even after the pericytes ware subjected to 72 hours of high glucose and are returned to low glucose conditions for another 72 hours, the SHP-1 expression level did not return to the constitutive level seen in the low-glucose only conditions, indicating glycemic memory, as shown in FIG. 5A.

Figure 5B:
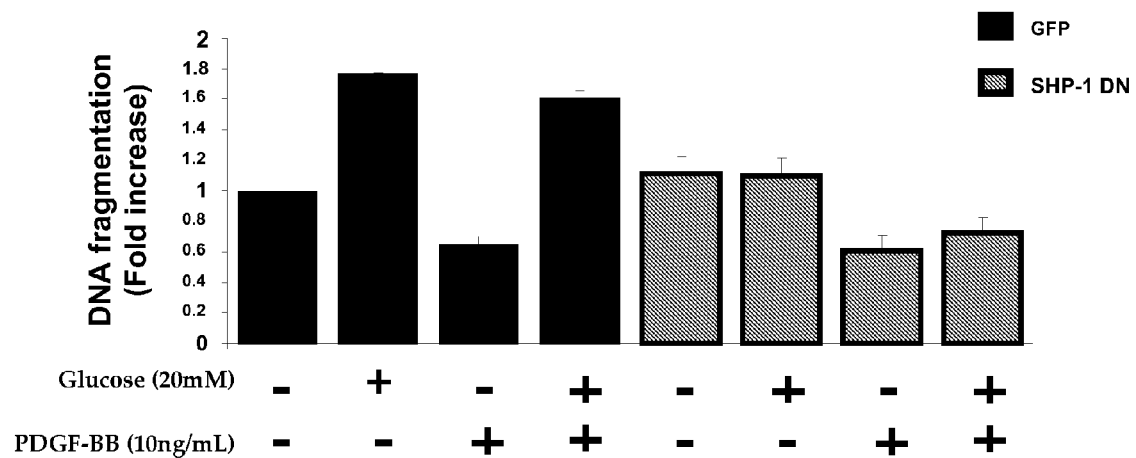
FIG. 5B is a bar graph showing the effects of a SHP-1 dominant negative on apoptosis in the presence and absence of high glucose or PDGF-BB.

This effect of SHP-1 on pericytes persists even in the presence of PDGF, which normally increases growth and survival in pericytes (FIG. 5B). A dominant negative form of SHP-1 (Dubois et al., Nat. Med. 12(5): 549-556 (2006)) reduces HG-induced apoptosis, even in the presence of PDGF (FIG. 5B).

Example 3

SHP-1 Expression in the Retina of Streptozotocin-Induced Diabetic Mice

Figure 6:
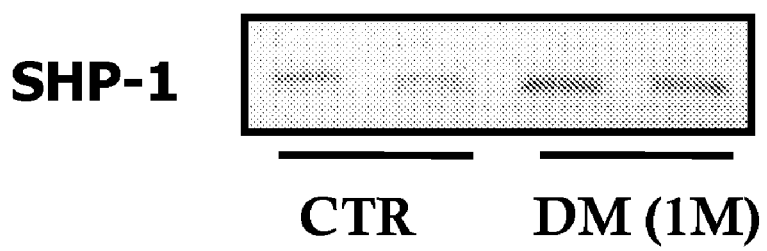
FIG. 6 is a Western Blot showing expression of SHP-1 in the retina of normal mice (CTRL) and mice with Streptozotocin-induced diabetes mellitus (DM) one month after induction of DM.

SHP-1 expression in a mouse model for diabetes (DM, streptozotocin-induced) was compared to control mice. An antibody directed against SHP-1 (Upstate) was used on prepared retinal tissue from control and diabetic mice (prepared as previously published, see Ishii et al., Science 272, 728-731 (1996)) according to manufacturer's instructions in a Western blot analysis. SHP-1 expression levels were greater in DM mice 1 month after streptozotocin induction than in control mice, as shown in FIG. 6.

Example 4

SHP-1 Expression Correlated with Phosphorylation of p38 MAPK in Diabetic Mouse Retina Studies of SHP-1 and p38 MAPK expression, and p38 MAPK phosphorylation in control and diabetic mice retina were done to characterize the relationship between p38MAPK and SHP-1. Antibodies directed against SHP-1, p38MAPK (Cell Signaling Technology, Inc., Danvers, Mass.) and phosphorylated p38MAPK (Cell Signaling Technology, Inc., Danvers, Mass.) were used on retinal tissue prepared from control and diabetic mice (prepared as previously published) according to manufacturer's instructions.

Figure 7:
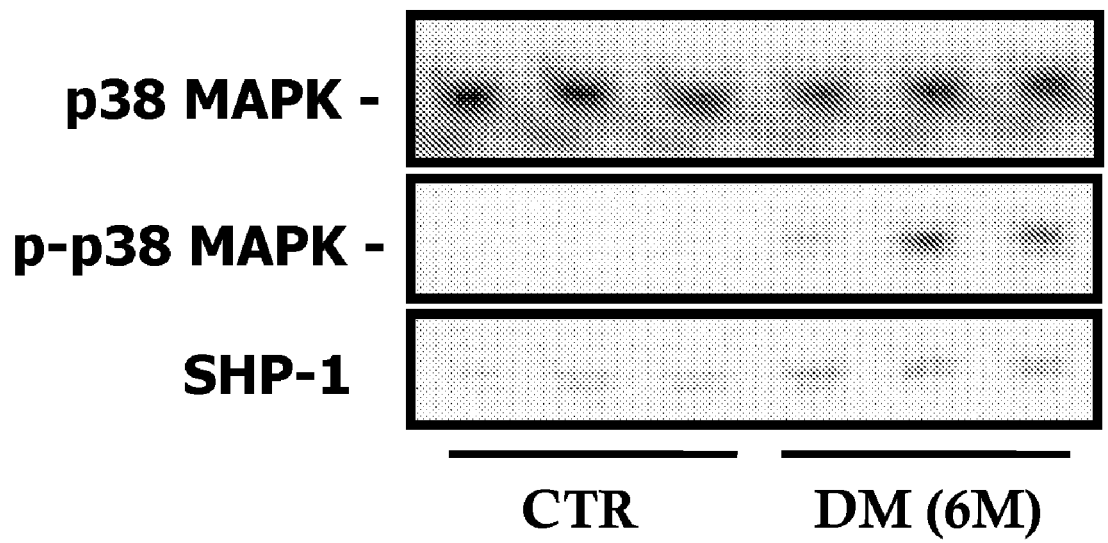
FIG. 7 is a Western Blot showing expression of p38MAPK, p-p38MAPK, and SHP-1 in normal mice (CTRL) and mice with Streptozotocin-induced diabetes mellitus (DM) six months after induction of DM, showing an increase in SHP-1 levels.

Expression levels of SHP-1 in DM mice 6 months after streptozotocin induction were increased compared to control mice, as shown in FIG. 7. Expression levels of p38 MAPK were similar in control and DM mice, but the level of phosphorylation of p38 MAPK was markedly increased in DM mice compared to control.

These results indicate that the increases in phospho-p38 and SHP-1 seen in the cultured pericytes also occur in vivo in an animal model of diabetes.

Example 5

Expression of SHP-1 in the Glomeruli of Control and Diabetic Rats

Figure 8:
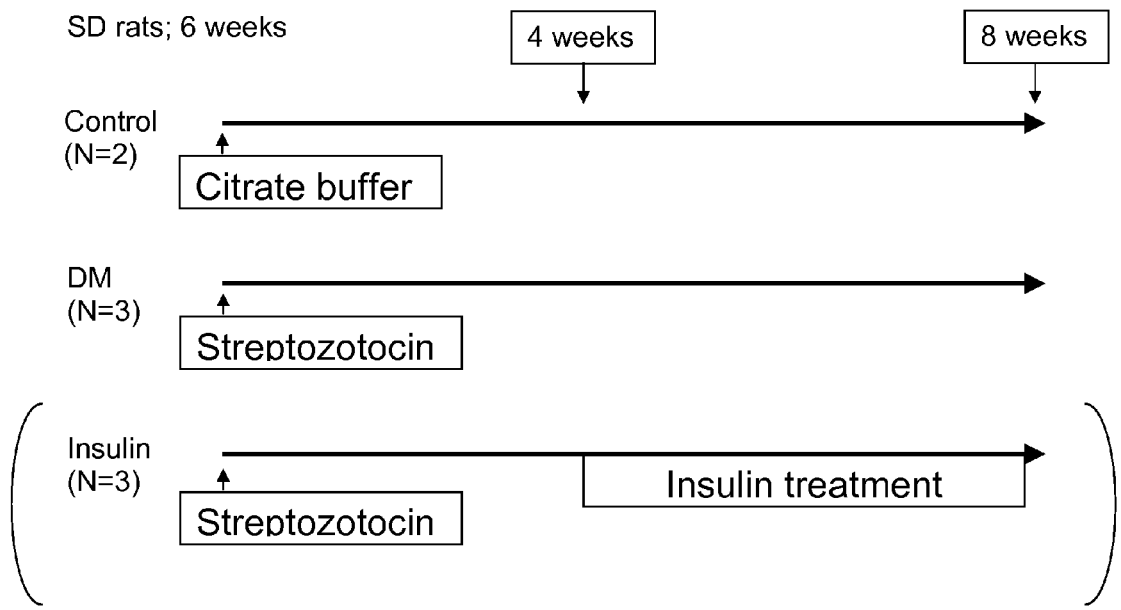
FIG. 8 is a schematic illustration of some of the treatment protocols used to generate control, DM, and insulin-treated rats.

The expression of SHP-1 was studied in the glomeruli of Sprague-Dawley rats (SD). Six-week old SD rats were either injected intraperitoneally with citrate buffer (n=2), streptozotocin (n=3), or streptozocin and later treated with insulin (n=3), as indicated in FIG. 8. After 8 weeks, the rats were sacrificed and glomeruli were prepared for Western blotting as previously published, using antibodies against SHP-1/2 and 13-actin.

Figure 9:
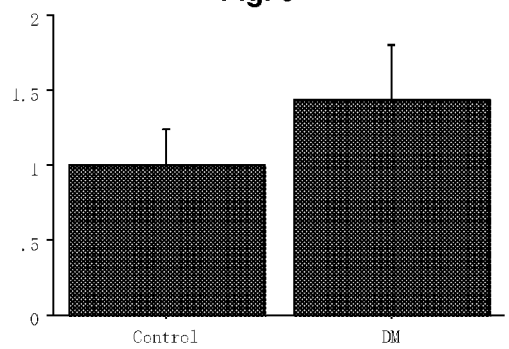
FIG. 9 is a bar graph.
Figure 10:
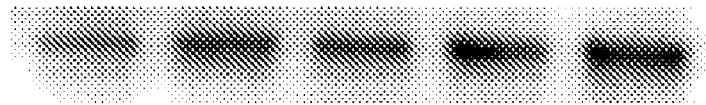
FIG. 10 is a Western blot, illustrating SHP-1 levels in the glomeruli in DM rats as compared to controls.
Figure 10:
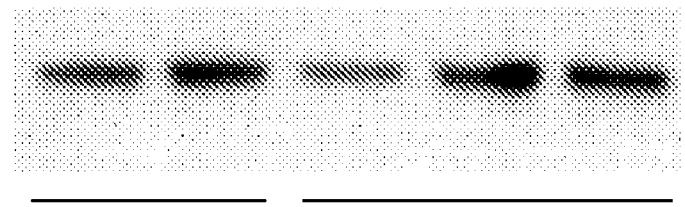

Expression of SHP-1 was upregulated in the glomeruli of the streptozotocin-treated SD rats, as compared to the control rats, as shown in FIGS. 9-10. These results indicate that SHP-1 is likely to be involved in the pathology of diabetic nephropathy.

Example 6

Phosphorylation Levels of Phospho-p38 MAPK in Glomeruli of Control and Diabetic Rats Correlates with Increased Expression of SHP-1/2

Figure 11:
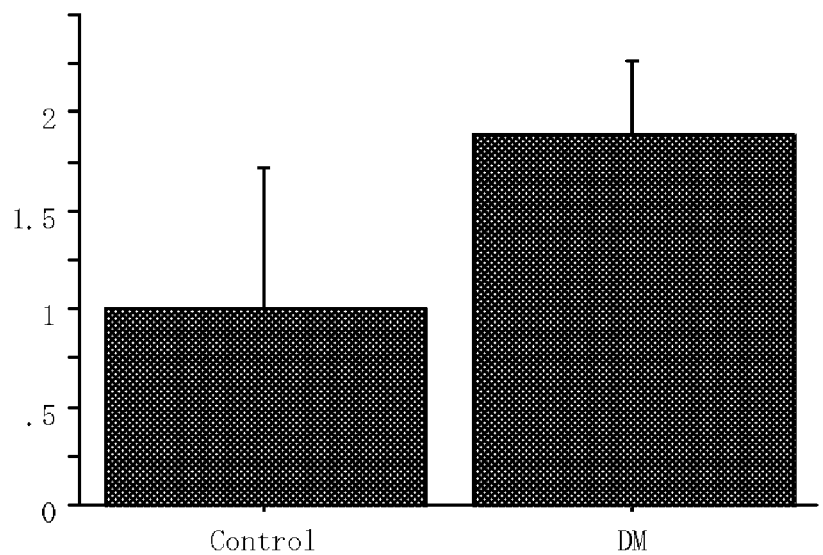
FIG. 11 is a bar graph.
Figure 12:
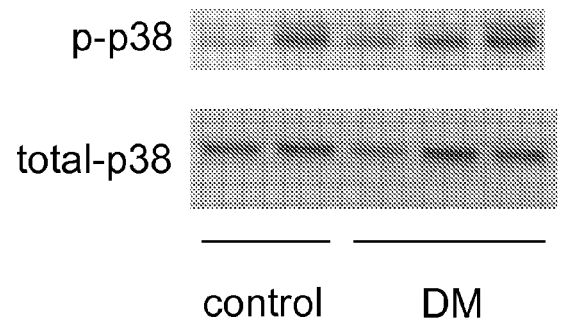
FIG. 12 is a Western blot, illustrating phospho-p38 levels in the glomeruli in DM rats as compared to controls.

The expression of total p38 MAPK and the phosphorylation levels of phospho-p38 MAPK were studied in the glomeruli of control and streptozotocin-induced diabetic rats, essentially as described in the above example. An antibody directed against p38 MAPK was used to assess the expression of total p38 MAPK, while an antibody specific to phosphorylated p38 MAPK was used to assess phosphorylation levels, as shown in FIGS. 11-12. More phospho-p38 MAPK was evident in the glomeruli of the diabetic rats than in the control, similar to the increased expression of SHP-1 as shown in FIGS. 11-12.

Example 7

P38 MAPKα Reduces HG-Induced Expression of SHP-1

Figure 14:
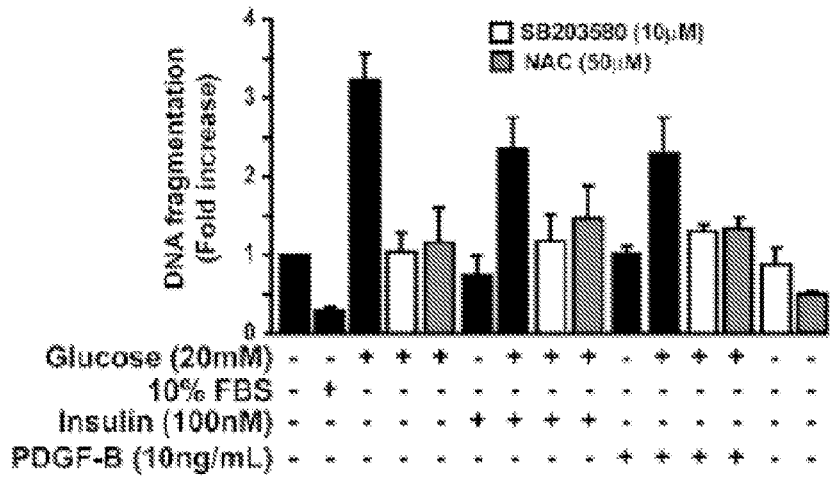
FIG. 14 is a bar graph showing the effects of high glucose, 10% fetal bovine serum (FBS), insulin, and PDGF-BB on apoptosis, in the presence and absence of an antioxidant (NAC) and an inhibitor of p38 MAPK.
Figure 15:
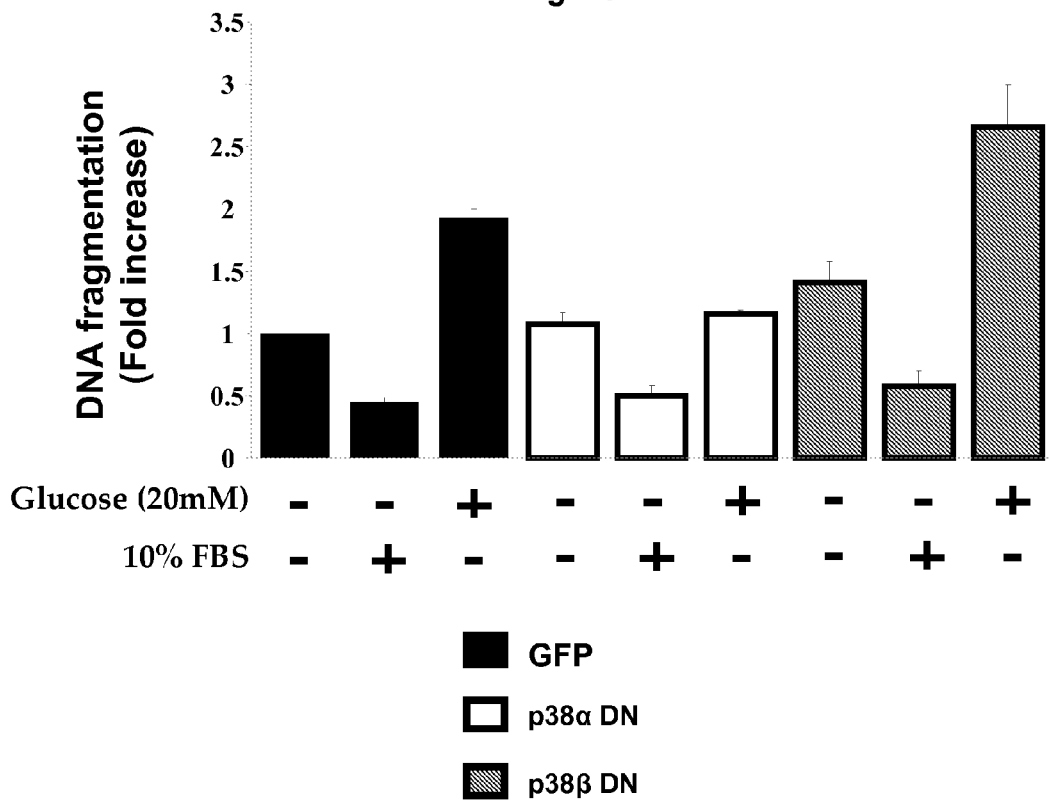
FIG. 15 is a bar graph showing apoptosis induced by high glucose in pericytes infected with dominant negative adenovirus of p38α (open bars) or β (grey bars) isoforms.

Expression of a dominant negative mutant of p38αMAPK (Wang et al., J. Biol. Chem., 273(4):2161-2168 (1998)), or co-treatment with the p38MAPK inhibitor SB203580, prevented apoptosis and abrogated PDGF-BB actions in pericytes (FIGS. 14 and 15). The dominant negative of p38 MAPK α reduces apoptosis in HG, whereas the dominant negative of p38 MAPK beta actually increased apoptosis in HG.

These results demonstrate that p38 MAPKα activation plays a part in HG-induced apoptosis, and therefore p38 MAPKα is a target for treatments for DN and DR.

Example 8

HG-Induced Expression of SHP-1 Blocks PDGF-Beta Receptor Phosphorylation by PDGF-BB Cultured pericytes were treated with high glucose (~20 mM glucose) and subsequently prepared for Western blot analyses as described in Example 2. An antibody directed against phosphorylated PDGF-Beta receptor was used to assess the effects of the HG treatment on receptor phosphorylation levels.

Figure 16:
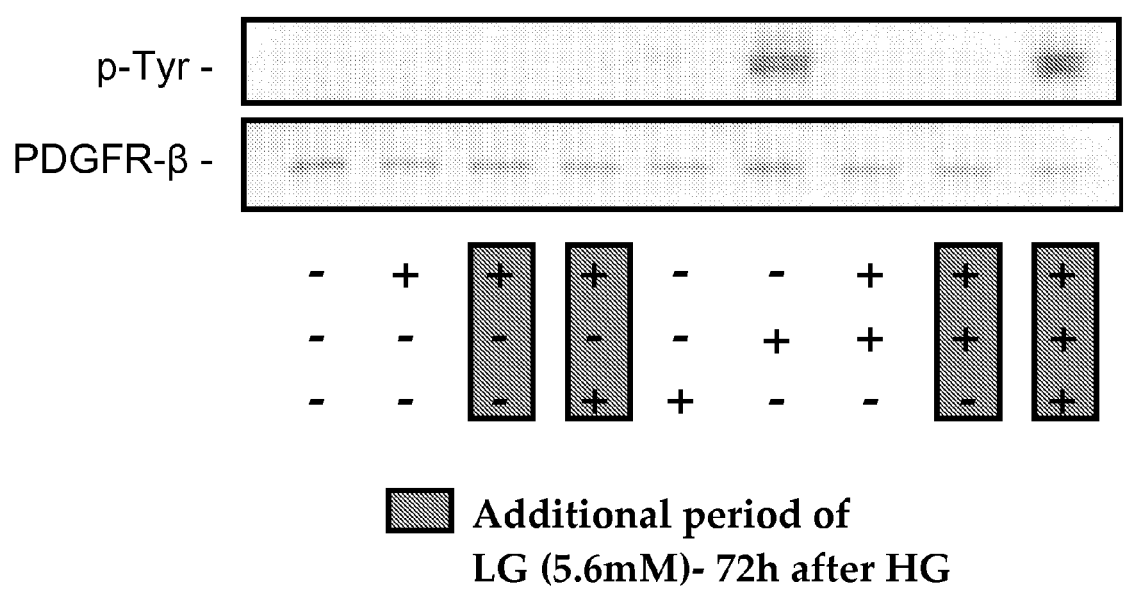
FIG. 16 is a Western blot showing that high glucose treatment prevented tyrosine phosphorylation of PDGFR-β induced by PDGF, and that this effect can be reversed by a p38 MAPK inhibitor (SB203580).

The results are shown in FIG. 16. In normal glucose, PDGF-R activation by PDGF results in increased phosphorylation of the phosphotyrosine site on the PDGF-R, indicating activation of the receptor. HG-induced expression of the protein tyrosine phosphatase SHP-1 blocked this phosphorylation of the PDGF-Beta receptor phosphorylation by PDGF-BB, reducing activation of the receptor, preventing PDGF-induced cell survival and increasing apoptosis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing or predicting risk of developing diabetic retinopathy, or diabetic nephropathy, or both, in a subject, the method comprising: identifying a subject suspected to have or be at risk of developing diabetic retinopathy, or diabetic nephropathy, or both; obtaining a biological sample from the subject; determining a level of SHP-1 protein or mRNA in the sample; and comparing the level of SHP-1 protein or mRNA in the sample to a predetermined reference level of SHP-1 protein or mRNA, wherein a level of SHP-1 protein or mRNA that is above the reference level indicates that the subject has or is at risk of developing diabetic retinopathy, or diabetic nephropathy, or both.

2. The method of claim 1, wherein the sample is selected from the group consisting of a biological fluid, a cell, and a tissue sample.

3. The method of claim 2, wherein the biological fluid is blood or urine.

4. The method of claim 2, wherein the cell is a cell from the retina, vitreous, or kidney of the subject.

5. The method of claim 2, wherein the tissue sample is from the kidney of the subject.

6. The method of claim 1, wherein the reference level is a level of SHP-1 protein or mRNA in a control subject unaffected by diabetic retinopathy, or diabetic nephropathy, or both.

7. The method of claim 1, wherein the reference level is a level of SHP-1 protein or mRNA in a subject affected by diabetic retinopathy, or diabetic nephropathy, or both.

8. The method of claim 7, wherein the subject has one or more symptoms associated with an elevated level of SHP-1 or the subject has diabetes.

* * * * *